US005674249A

United States Patent [19]
de Coriolis et al.

[11] Patent Number: 5,674,249
[45] Date of Patent: Oct. 7, 1997

[54] ATRIAL DEFIBRILLATION SYSTEM HAVING A PORTABLE COMMUNICATION DEVICE

[75] Inventors: Paul E. de Coriolis, Bellevue; Joseph M. Bocek, Seattle; Barry M. Yomtov, Issaquah, all of Wash.

[73] Assignee: InControl, Inc., Redmond, Wash.

[21] Appl. No.: 641,976

[22] Filed: May 2, 1996

[51] Int. Cl.$^6$ ........................................... A61N 1/39
[52] U.S. Cl. ................... 607/5; 607/32; 607/60; 128/903
[58] Field of Search ..................... 607/5, 30–32, 607/60; 364/514

[56] References Cited

U.S. PATENT DOCUMENTS

| | | | |
|---|---|---|---|
| 5,311,449 | 5/1994 | Adams | 364/514 |
| 5,336,245 | 8/1994 | Adams et al. | 607/32 |
| 5,342,408 | 8/1994 | de Coriolis et al. | 607/32 |

*Primary Examiner*—Jeffrey R. Jastrzab
*Attorney, Agent, or Firm*—Richard O. Gray, Jr.

[57] ABSTRACT

An atrial defibrillation system includes an implantable atrial defibrillator including an atrial fibrillation detector and an atrial cardiovertor, and an external communication device dimensioned to be hand-held and including an RF transmitter for transmitting a command signal to the implanted defibrillator. The implantable defibrillator includes a receiver for receiving the command signal, activation means responsive to receipt of the command signal for activating the atrial fibrillation detector and the atrial cardiovertor if the atrial fibrillation detector detects atrial fibrillation, and an RF transmitter for transmitting an acknowledgment signal to the external communication device responsive to the receiver receiving the command signal. The external communication device further includes a receiver for receiving the acknowledgment signal and an indicator for providing a perceptible indication responsive to receipt of the acknowledgment signal.

10 Claims, 2 Drawing Sheets

ATRIAL DEFIBRILLATION SYSTEM HAVING A PORTABLE COMMUNICATION DEVICE

BACKGROUND OF THE INVENTION

The present invention generally relates to a defibrillation system including an atrial defibrillator for applying cardioverting electrical energy to the atria of a human heart in need of cardioversion. The present invention is more particularly directed to such a system having a portable communication device capable of communicating with the implantable atrial defibrillator to initiate atrial fibrillation therapy or to select different therapy modalities.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart, and may even experience dizziness or even loss of consciousness.

Atrial fibrillation occurs suddenly, and many times can only be corrected by a discharge of electrical energy to the heart. Implantable atrial defibrillators have become a reality to provide relief to patients suffering from occurrences of atrial fibrillation For example, implantable atrial defibrillators and lead systems which exhibit complete automatic operation are fully described in U.S. Pat. No. 5,282,837, issued Feb. 1, 1994, for "Improved Atrial Defibrillator and Method", U.S. Pat. No. 5,350,404, issued Sep. 27, 1994, for "Lead System for Use with an Atrial Defibrillator and Method", and U.S. Pat. No. 5,207,219, issued May 4, 1993, for "Atrial Defibrillator and Method for Providing Interval Timing Prior to Cardioversion", all of which patents are assigned to the assignee of the present invention and incorporated herein by reference. Each of these patents discloses and claims an implantable atrial defibrillator wherein atrial fibrillation is automatically detected and, when needed, cardioverting electrical energy is applied to the atria to terminate the atrial fibrillation episode and return the heart to normal sinus rhythm.

As with any implantable device, it would be desirable to be able to provide the patient with some manual control for the implanted device. For example, implantable pacemakers known in the art may be totally deactivated by placing a magnet over the implant site. The magnetic field of the magnet causes a reed switch within the implanted device to remain either open or closed as long as the magnet is held there. Other magnet modes are known for checking the power levels of the implanted device battery, for example.

While magnets have proven effective in the past, they are not convenient to use. First of all, such magnets are heavy and, in most uses, rather large, making them difficult to carry in a pocket or purse. Also, because the magnets produce a magnetic field, they can erase dictation or other type of audio tape to which they may come into close proximity with in a purse or pocket. Under such conditions, they can also erase the magnetic strips on credit and bank cards. They would further erase floppy disks for computers.

Providing some manual control over an implanted atrial defibrillator is described in U.S. Pat. No. 5,490,862. There, a magnet is described for generating external commands which cause the defibrillator to enter a therapy sequence. A magnet is certainly effective for such use. However, in addition to the drawbacks previously mentioned, magnets do not provide any means for feedback to inform the patient that the implanted device is acting upon the external command. An acknowledgment of receipt of a command and the fact that the implant is implementing the command would be important feedback to patients. This is especially true if the patient is attempting to have the implanted device initiate much needed therapy.

SUMMARY OF THE INVENTION

The invention provides an atrial defibrillation system including an implanted atrial defibrillator including therapy intervention means for detecting and cardioverting atrial fibrillation, and an external communication device dimensioned to be hand-held and including an RF transmitter for transmitting a command signal to the implantable defibrillator. The implantable defibrillator includes a receiver for receiving the command signal, means for performing a task responsive to receipt of the command signal and an RF transmitter for transmitting an acknowledgment signal to the external communication device responsive to the receiver receiving the command signal. The external communication device further includes a receiver for receiving the acknowledgment signal and an indicator for providing a perceptible indication responsive to receipt of the acknowledgment signal.

The invention also provides an atrial defibrillation system including an implantable atrial defibrillator including an atrial fibrillation detector and an atrial cardiovertor to form a therapy invention means, and an external communication device dimensioned to be hand-held and including an RF transmitter for transmitting a command signal to the implanted defibrillator. The implantable defibrillator includes a receiver for receiving the command signal, activation means responsive to receipt of the command signal for activating the atrial fibrillation detector and the atrial cardiovertor if the atrial fibrillation detector detects atrial fibrillation, and an RF transmitter for transmitting an acknowledgment signal to the external communication device responsive to the receiver receiving the command signal. The external communication device further includes a receiver for receiving the acknowledgment signal and an indicator for providing a perceptible indication responsive to receipt of the acknowledgment signal.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
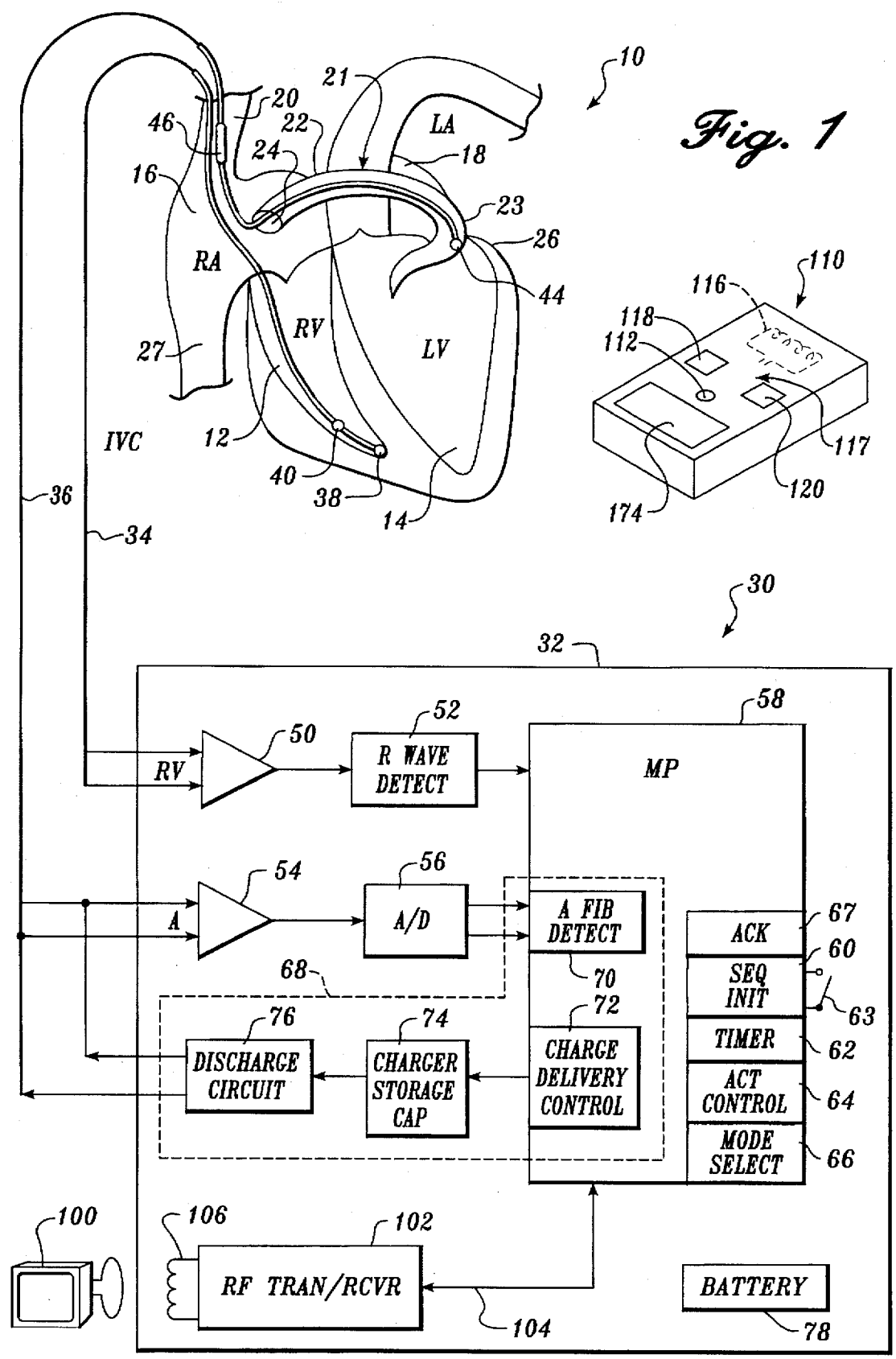
FIG. 1 is a block diagram of an atrial defibrillation system embodying the present invention.

Referring now to FIG. 1, it illustrates an atrial defibrillation system 10 embodying the present invention including an implantable atrial defibrillator 30 shown in association with a schematically illustrated human heart in need of atrial fibrillation monitoring and potential cardioversion and a portable, hand-holdable external communication device 110. The portions of the heart illustrated in FIG. 1 are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart. The electrodes 38 and 40 permit bi-polar sensing of ventricular activations in the right ventricle. As illustrated, the lead 34 is preferably fed through the superior vena cava 20, into the right atrium 16 and then into the right ventricle 12, as illustrated.

The second lead 36 generally includes a first or tip electrode 44 and a second or proximal electrode 46. As illustrated, the second lead 36 is flexible and arranged to be passed down the superior vena cava 20, into the right atrium 16, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16.

The first electrode 44 together with the second electrode 46 provide bi-polar sensing of heart activity in the atria 16 and 18. The first electrode 44 and the second electrode 46 further provide for the delivery of defibrillating or cardioverting electrical energy to the atria.

Within the enclosure 32, the atrial defibrillator 30 includes a first sense amplifier 50, an R wave detector 52, and a second sense amplifier 54. The first sense amplifier 50 and the R wave detector 52, together with electrodes 38 and 40 of lead 34, sense ventricular activations of the right ventricle 12. The second sense amplifier 54, together with the first electrode 44 and second electrode 46 of the second lead 36, detect atrial activity of the heart.

The output of the first sense amplifier 50 is coupled to the R wave detector 52. The R wave detector 52 is of the type well known in the art which provides an output pulse upon the occurrence of an R wave being sensed during a cardiac cycle of the heart. The output of the second sense amplifier 54 is coupled to an analog-to-digital convertor 56 which converts the analog signal representative of the atrial activity of the heart being detected to digital samples for further processing in a manner to be described hereinafter.

The enclosure 32 of the atrial defibrillator 30 further includes a microprocessor 58. The microprocessor 58 is preferably implemented in a manner as described in U.S. Pat. No. 5,490,862, issued Feb. 12, 1996 and which is incorporated herein by reference. The implementation of the microprocessor 58 in accordance with this embodiment of the present invention results in a plurality of functional stages. The stages include a sequence initiating stage 60, a timer 62, an activation control stage 64, a mode select stage 66, an acknowledgment stage 67, an atrial fibrillation detector 70, and a charge and delivery control stage 72.

The microprocessor 58 is arranged to operate in conjunction with a memory (not shown) which may be coupled to the microprocessor 58 by a multiple-bit address bus (not shown) and a bi-directional multiple-bit data bus (not shown). This permits the microprocessor 58 to address desired memory locations within the memory for executing write or read operations. During a write operation, the microprocessor stores data and operating parameters (such as a selected modality) in the memory at the addresses defined by multiple-bit addresses conveyed over the address bus and conveys the data to the memory over the multiple-bit data bus. During a read operation, the microprocessor 58 obtains data from the memory at the storage locations identified by the multiple-bit addresses provided over the address bus and receives the data from the memory over the bi-directional data bus.

For entering operating parameters into the microprocessor 58, such as mode selection, the microprocessor 58 receives programmable operating parameters, such as mode commands, from an external controller 100 which is external to the skin of the patient. The external controller 100 is arranged to communicate with a receiver/transmitter 102 which is coupled to the microprocessor 58 over a bi-directional bus 104. The receiver/transmitter 102 may be of the type well known in the art for conveying various information which it obtains from the microprocessor 58 to the external controller 100 or for receiving programming parameters, such as mode commands, from the external controller 100 which the receiver/transmitter 102 then conveys to the microprocessor 58 for storage in the aforementioned external memory within enclosure 32.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One preferred communication system is disclosed, for example, in U.S. Pat. No. 5,342,408, which is incorporated herein by reference.

The receiver/transmitter 102 may also communicate with the portable communication device 110. However, the parameters which may be provided by the device 110 are preferably vastly limited as compared to the parameters which may be derived from the external programmer. To that end, the parameters which may be communicated from the device 110 are preferably simple mode select commands and a therapy sequence control command to initiate therapy. The mode select commands preferably set the defibrillator into one of a number of modalities wherein each modality is determined and controlled by parameters which can only be selected by a physician operating the external programmer 100.

In accordance with the present invention, the acknowledgment stage 67 formats an acknowledgment when the defibrillator 30 receives a command from the device 110. The acknowledgment is transmitted by the transmitter/receiver 102 to cause an indicator, such as a light emitting diode 112 (LED) to provide a readily perceptible indication that the command was received. This provides positive feed-back for the patient which has not been possible with prior art magnets. Hence, the patient will positively know if the command was received and is being acted upon by the implanted device 30.

The atrial defibrillator 30 further includes an intervention sequencer 68 which performs an intervention sequence task, including atrial fibrillation detection and cardioversion of the atria (if necessary). To that end, the intervention sequencer includes the previously mentioned atrial fibrillation detector 70 and charge and delivery control 72, and a charger and storage capacitor circuit 74 and a discharge circuit 76.

Each intervention sequence is begun by the sequence initiating stage 60 receiving a sequence command. The sequence command may be generated by either a magnet generating a magnetic field to temporarily closed reed switch 63 or by the communication device generating an RF signal to be received by receiver/transmitter 102 in accordance with this preferred embodiment. When the intervention sequencer 68 is not performing an intervention sequence, it is held in a deactivated or inactive state by the activation control stage 64. When an intervention sequence is to be performed, the sequence initiating stage 60 overrides the activation control stage 64 to cause the intervention sequencer to perform an intervention sequence.

Each intervention sequence preferably begins with the sequence initiating stage 60 causing the atrial fibrillation detector 70 to determine if the atria are in need of cardioversion. This analysis is preferably performed on data obtained from sense amplifier 54 and analog-to-digital convertor 56, which is prestored in the aforementioned memory (not shown) external to the microprocessor 58, but contained within the implantable enclosure 32. The atrial fibrillation detector 70 may alternatively be of the type which performs real time analysis of the data provided by the analog-to-digital convertor 56.

If the atria are in fibrillation, and hence in need of cardioversion, the charger and storage capacitor circuit 74 under control of the charge and delivery stage 72 charges its storage capacitor to a predetermined voltage level for cardioverting the atria of the patient's heart. When the capacitor of circuit 74 is charged, the charge and delivery control stage 72 then causes the discharge circuit 76 to discharge the storage capacitor within circuit 74 for a predetermined time to provide a controlled discharge of cardioverting electrical energy to the atria of the heart. To that end, the discharge circuit 76 is coupled to the first electrode 44 and the second electrode 46 of the second lead 36 for applying the cardioverting or defibrillating electrical energy to the atria. The discharge is preferably initiated in timed relation to an R wave detected by sense amplifier 50 and R wave detector 52. Interval timing prior to energy delivery is also preferably performed as taught in U.S. Pat. No. 5,207,219.

Lastly, the defibrillator 30 includes a depletable power source 78, such as a lithium battery. The battery 78, of course, provides power to the electrical components of the atrial defibrillator 30.

The overall operation of the atrial defibrillator 30 is preferably carried out as described in U.S. Pat. No. 5,490,862, incorporated herein by reference. As described in that patent, the atrial defibrillator 30 is first placed into one of a plurality of different modes of operation. The selectable modalities include an automatic mode, a patient activated mode, and a combined automatic and patient activated mode. To that end, at relatively short, predetermined time intervals, the RF transmitter/receiver 102 is activated to determine if either the external controller 100 or the communication device 110 is attempting to communicate with the implanted defibrillator 30. If a program mode control signal is being received, the mode select stage 66 will cause the acknowledge stage 67 to format and transmit an acknowledgment, decode the mode command and set the defibrillator 30 into the selected mode of operation.

The mode select stage 66 first determines if the received program mode command corresponds to the automatic mode. If it does, it then sets the microprocessor 58 in the automatic mode for obtaining those programs instructions from the external memory which correspond to the automatic mode of operation. If it is determined that the received program mode command does not correspond to the automatic mode, the mode select stage 66 then determines if the received program mode command corresponds to the patient activated mode. If it does, the mode select stage 66 then sets the microprocessor into the patient activated mode for obtaining those operating instructions from the external memory which correspond to the patient activated mode. If the mode select stage 66 determines that the received program mode command does not correspond to the patient activated mode, it then sets the microprocessor into the combined automatic and patient activated mode. This will cause the microprocessor to obtain those operating instructions from the external memory which correspond to the combined automatic and patient activated mode.

If the atrial defibrillator 30 is set into the automatic mode by the mode select stage 66, the atrial defibrillator 30 will enter the automatic mode. It will automatically, at predetermined times, determine if the atria are in fibrillation. If the atria are in fibrillation, cardioverting electrical energy is applied to the atria until the atrial fibrillation episode is terminated or until a predetermined number of cardioversion attempts are made.

If the patient activated mode is selected, the sequence initiating stage 60 continuously detects for a sequence command generated from external to the patient. When the sequence command is received by the implanted device, the sequence command will have been detected and the sequence initiating stage causes the intervention sequence to be performed. The atrial fibrillation detector 70 first determines if the atria are in fibrillation and in need of cardioversion. If the atria are not in fibrillation, the process is terminated and the sequence initiating stage once again waits for another sequence command. However, if atria are in fibrillation, cardioverting electrical energy is applied to the heart. After the cardioverting electrical energy is applied to the heart, the atrial fibrillation detector 70 determines if the atrial fibrillation episode has been terminated. If it has, the process is terminated and the sequence initiating stage once again waits for another sequence command. When the sequence initiating stage is detecting for a sequence command, the activation control stage 64 maintains the intervention sequencer 68 in the deactivated state. If the atrial fibrillation continues, the atria are once again cardioverted. This process continues until the atrial fibrillation episode is either terminated or until a predetermined number of cardioversion attempts have been made.

Lastly, if the atrial defibrillator is programmed into the combined automatic and patient activated mode the sequence initiating stage 60 continuously waits for a sequence command or for the timer 62 to time out. When either occurs of the sequence initiating stage 60 will cause the intervention sequencer 68 to perform its intervention sequence as previously described.

Turning now more particularly to the communication device 110 of FIG. 1, in addition to the LED 112, it includes a liquid crystal display (LCD) 114, a coil antenna 116, and a plurality of press switches 117 including press switches 118 and 120. The LCD 114 may be used for displaying short messages indicating modalities available for selection, current modality, and receipt of a therapy initiation command or modality selection by the implanted device. The coil antenna 116 may be used for both transmitting and receiving RF signals. The push switches are provided by selecting a modality by pressing switch 118 and sending a sequence command to initiate therapy by pressing switch 120.

Figure 2:
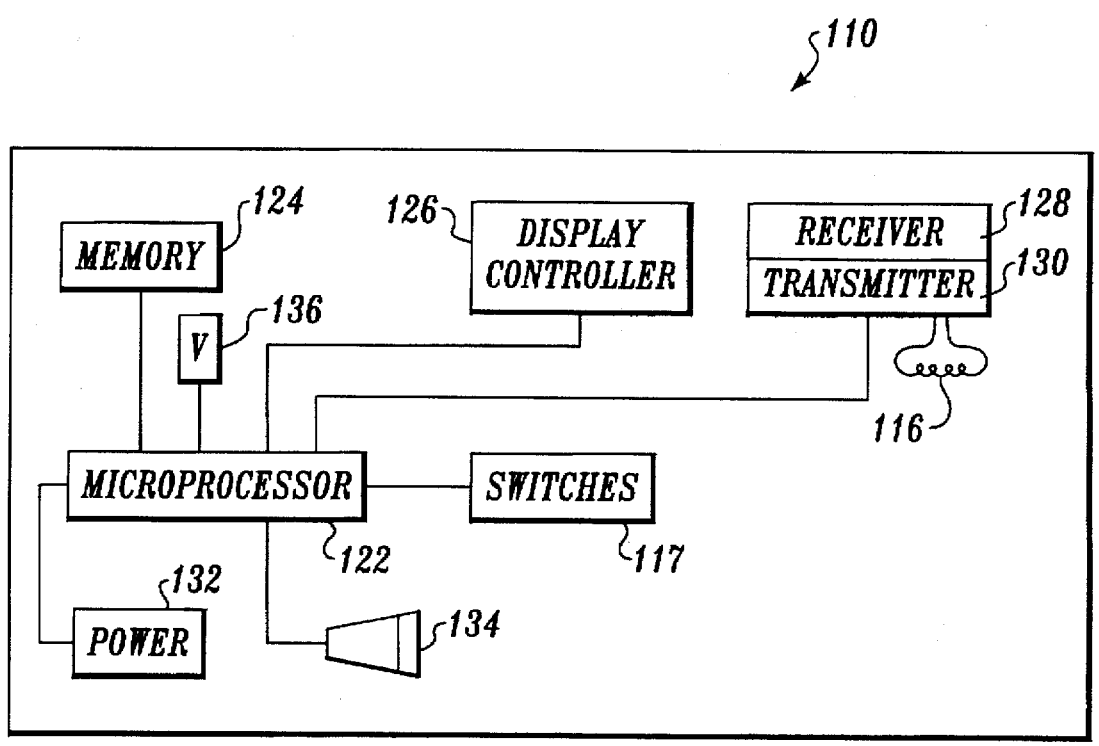
FIG. 2 is a block diagram of a portable communication device which may be used in practicing the present invention.

FIG. 2 is a block diagram of the communication device 110. It includes a microprocessor 122, a memory 124, a display controller 126, a receiver 128 and transmitter 130, the coil antenna 116, the switches 117, and a battery power source 132.

The microprocessor 122 controls the overall functioning of the device 110 by performing operations defined by operating instructions stored in memory 124. The instructions stored in memory 124 preferably include instructions defining a communication protocol compatible with the implantable device 30. The display controller 126 controls the LED 112 and the LCD 114 of the communication device 110 in a manner known in the art. The receiver 128 and transmitter 130 are controlled by the microprocessor 122 for communicating with the receiver/transmitter 102 of the implanted device 30 when required.

Whenever the transmitter 130 sends a command to the implanted device 30, it will expect an acknowledgment from the implanted device that the command was received and is being acted upon. When the acknowledgment is received by receiver 128, the display controller causes the LED 112 to light-up so as to be readily discernible. To further that end, the LED 112 may be caused to blink on and off by the display controller 126. Also a short message may also be displayed on the LCD 114 to further indicate that the command was received and the type of command or mode selection made. Alternatively, the indicator may be a small speaker 134 to produce an audible sound or a vibrator 136 to produce a discernible vibration. All of the foregoing provides positive feedback to the patient when making an external command not previously available in the prior art. This positive feedback includes both an acknowledgment that the command was reached and a description of the task being performed responsive to the command.

While a particular embodiment of the present invention has been shown and described, modifications may be made. Hence, it is therefore intended in the appended claims to cover all such changes and modifications which fall within the true spirit and scope of the invention.

What is claimed is:

1. An atrial defibrillation system comprising:

an implantable atrial defibrillator including at least one lead having electrode means for sensing atrial activity of a heart and applying cardioverting electrical energy to atria of the heart, an atrial fibrillation detector responsive to the sensed atrial activity, and a cardioverter for providing the cardioverting electrical energy; and a portable external communication device dimensioned to be entirely hand-held and including an RF transmitter for transmitting a command signal to cause the implantable defibrillator to initiate the performance of a task, the implantable defibrillator including a receiver for receiving the command signal, means for performing the task responsive to receipt of the command signal, means for generating an acknowledgment signal to acknowledge receipt of the command signal and the initiation of the performance of the task, and an RF transmitter for transmitting the acknowledgment signal to the external communication device, and the external communication device further including a receiver for receiving the acknowledgment signal and an indicator for providing a perceptible indication responsive to receipt of the acknowledgment signal.

2. A system as defined in claim 1 wherein the means for performing a task comprises therapy intervention means including the atrial fibrillation detector and the atrial cardioverter for performing the task of detecting and cardioverting atrial fibrillation.

3. A system as defined in claim 1 wherein the means for performing a task includes an operating mode selection.

4. A system as defined in claim 1 wherein the indicator is a visible light producing device.

5. A system as defined in claim 1 wherein the indicator is a light emitting diode.

6. A system as defined in claim 1 further including a display for displaying a message.

7. A system as defined in claim 1 further including a display for indicating the task being performed in response to the command signal.

8. A system as defined in claim 1 wherein the indicator is an audible sound producing device.

9. A system as defined in claim 1 wherein the indicator is a vibration producing device.

10. An atrial defibrillation system comprising:

an implantable atrial defibrillator including an atrial fibrillation detector, an atrial cardioverter, and electrodes attached to the atrial cardioverter; and a portable external communication device dimensioned to be hand-held and including an RF transmitter for transmitting a command signal to the implantable defibrillator, the implantable defibrillator including a receiver for receiving the command signal, activation means responsive to receipt of the command signal for activating the atrial fibrillation detector and the atrial cardioverter if the atrial fibrillation detector detects atrial fibrillation, means for generating an acknowledgment message responsive to the receiver receiving the command signal and an RF transmitter for transmitting the acknowledgment message to the external communication device, and the external communication device further including a receiver for receiving the acknowledgment message and an indicator for providing a perceptible indication responsive to receipt of the acknowledgment message.

* * * * *